United States Patent [19]

Ax et al.

[11] 4,296,201

[45] Oct. 20, 1981

[54] METHODS FOR THE DETECTION OF ANTIMITOCHONDRIAL AND ANTINUCLEAR ANTIBODIES

[75] Inventors: Wolfgang Ax, Marburg an der Lahn; Hartwig W. Bauer, Munich; Hans-Harald Sedlacek, Marburgh an der Lahn, all of Fed. Rep. of Germany

[73] Assignee: Behringwerke Aktiengesellschaft, Marburg an der Lahn, Fed. Rep. of Germany

[21] Appl. No.: 67,003

[22] Filed: Aug. 16, 1979

[30] Foreign Application Priority Data

Aug. 19, 1978 [DE] Fed. Rep. of Germany ....... 2836362

[51] Int. Cl.³ ............................................. G01N 33/54
[52] U.S. Cl. ........................................... 435/7; 424/8; 424/12; 435/29; 23/230 B

[58] Field of Search ...................... 435/240/241, 7, 29, 435/212; 23/230 B; 424/85, 87, 12, 8

[56] References Cited

U.S. PATENT DOCUMENTS

| | | | |
|---|---|---|---|
| 3,983,004 | 9/1976 | Trobisch et al. | 435/212 |
| 4,017,361 | 4/1977 | Febvre | 435/241 |
| 4,059,486 | 11/1977 | Tolbert | 435/241 |
| 4,172,124 | 10/1979 | Koprowski et al. | 435/240 |
| 4,209,587 | 6/1980 | Tolbert et al. | 435/29 |

OTHER PUBLICATIONS

Phillips et al.; International Journal Cancer: vol. 17, pp. 549–558, (1976).

*Primary Examiner*—Benoît Castel
*Attorney, Agent, or Firm*—Curtis, Morris & Safford

[57] ABSTRACT

What is disclosed are methods for the detection of antimitochondrial and antinuclear antibodies employing hypernephroma cells as a diagnostic agent.

2 Claims, No Drawings

METHODS FOR THE DETECTION OF ANTIMITOCHONDRIAL AND ANTINUCLEAR ANTIBODIES

The invention relates to methods for the detection of antimitochondrial and antinuclear antibodies.

Auto-immune diseases are characterized by the occurence of antibodies against cell constituents, for example nuclear proteins, DNA, and mitochondria.

The antinuclear and antimitochondrial factors are important insofar as they may be used as diagnostic and course-controlling agents for auto-immunity phenomena such as liver diseases, malignoms, drug intoxications and collagenoses.

Diagnostics for proving anti-nuclear antibodies are known. Also, a diagnostic agent for the detection of anti-mitochondrial antibodies is known. These diagnostics are employed, in principle, according to the indirect or double antibody method in which frozen cuts of liver or spleen or cells of blood or organs of various species are used as the substrate and labeled antibodies directed against antigenic determinants of the sought anti-bodies as are used as diagnostic antibodies [Nakumura, R. M., Chisari, F. V.; Edgingbon, T. S. (1975), Laboratory tests for diagnosis of autoimmune disease. In: M. Stefanini: Progress in Clinical Pathology, pages 177–203, Grune and Stratton, New York]. However, they have the disadvantage of being unstable. So, new preparations from freshly isolated organs or cells must continually be prepared. Another disadvantage is the low quantity of antigens in the various preparations which renders an exact diagnosis difficult.

Hence, there was a need for a diagnostic agent which does not have the aforementioned disadvantages and which permits the detection and determination of both kinds of antibodies.

Now, we have found that, surprisingly, the cells of malignant renal tumors, in particular those of hypernephroma, are particularly suited for this purpose.

Accordingly, the object of the invention is a diagnostic agent aimed at the delection of anti-mitochondrial as well as anti-nuclear antibodies, which is characterized by consisting essentially of the said specific cells and, further, to a diagnostic method wherein hypernephroma cells are used as the substrate cells.

These cells can be multiplied in cell cultures, for example according to the methods originated by R. Dulbecco and M. Vogt (J.Exp. Med. 99: 167, 1954), C. Rappaport (Bull. World Health Org. 14: 147, 1956) and E. Y. Lasfargues (Exper. Coll. Res. 13: 553, 1957).

The cells grow as an epithelium which spreads out flat and forms a cell monolayer that adheres to the surface of culture vessels. The cells may also be multiplied directly on slides on which they form, in similar manner, a cell monolayer.

The nuclei of the cells are distinctly visible and also the nucleoli, in contradistinction to other known tissue culture cells. This property renders them particularly suitable for proving anti-nuclear antibodies.

Furthermore, the cells are distinguished by great, outstretched mitochondria that make them suitable for proving anti-mitochondrial antibodies.

Cells which are suitable according to the invention may be obtained from a renal tumor, for example, in the following manner:

Fresh material of a renal tumor, isolated after surgery under sterile conditions and transported in a physiological medium, is mechanically comminuted, enzymatically disintegrated and the hypernephroma cells are multiplied in a tissue culture. For this purpose, it is advantageous to suspend the small tissue pieces (about 1 mm$^3$) obtained after surgery in a calcium-free and magnesium-free salt solution and to wash them by stirring with a magnetic stirrer. The washing liquid is rejected. Subsequently, a solution of collagenase in a physiological salt solution without calcium and magnesium is added to the small pieces and the whole is then stirred for about 15 minutes. The supernatant is recovered and a trypsin solution of 0.25% strength in a calcium- and magnesium-free medium, heated to 37° C., is added and the whole is stirred for about 15 minutes. The supernatant is isolated and the sediment is stirred again for 15 minutes with the trypsin solution and the supernatant is isolated. This process can be repeated several times. The supernatants are centrifuged each time at 200×g and dissolved in a tissue culture medium with addition of 20% of fetal calf serum.

10 ml portions of the cell suspension so isolated are seeded/plated as a primary culture in Petri dishes or screw-top bottles, expecially in bottles of a plastic material. The seeding in Petri dishes is effected under a moist atmosphere at 37° C. and regulation of the pH-value by supply of $CO_2$.

The cells are multiplied as follows:

As soon as a closed or almost closed monolayer has formed in the primary cultures, the cells are isolated from the monolayer of the primary culture by treating them with the enzymes of a trypsin solution, suspended in a fresh tissue culture medium and again seeded into new culture vessels. Upon corresponding dilution of the cell suspension to be proliferated, at least 3 daughter cultures are formed from one Petri dish having a closed monolayer. These 3 daughter cultures of the first passage, suitably in Petri dishes, show such a dense growth after 2–3 days that they can be passaged again.

Whereas primary cultures can be cultivated in Petri dishes made of a plastic material (10 cm diameter) or screwcap bottles of a plastic material (10 ml of usable capacity), greater cell quantities can be prepared in suitable, larger bottles of glass or a plastic material and other devices for mass culture.

The cells can be established on glass or plastic surfaces, such as cover glasses, slides or at the bottom of plates for micro-cultures, in amounts which are suitable for diagnostic purposes.

The hypernephroma cells can be passaged without difficulty up to the 50th passage. They can be stored according to known processes in liquid nitrogen at −196° C. and kept viable.

For proving antinuclear antibodies, it is recommended to fix the cells. This is carried out with known fixation agents, for example formalin, acetone, methanol, ethanol, or mixtures thereof, preferably with acetone, in a manner known from the literature, J. Lenng Tack et al., Arch. Derm. Forsch. 247, 161–170, (1973).

For proving antimitochondrial antibodies, the fixation must be omitted, since it destroys the corresponding antigenic determinants at the mitochondria.

The proof of the anti-mitochondrial or anti-nuclear anti-bodies is carried out as follows:

1. Detection and proof of antimitochondrial antibodies

The slides coated with air-dried, unfixed hypernephroma cells are over-coated with the antibody to be tested, dissolved in any desired isotonic salt solution, for example a phosphate-buffered NaCl-solution of 0.9% strength and incubated for 10 minutes to 2 hours, preferably 30 minutes, in a moist chamber. They are subsequently washed thoroughly, as far as possible 1 to 6 times, preferably 3 times, with an isotonic salt solution. The slides are then overcoated with a fluorescently-labeled antibody which is directed against antigen-determinants of the antibody sought for, in a dilution which excludes unspecific reactions with the hypernephroma cells. They are then incubated for 10 minutes to 2 hours, preferably for 30 minutes, in a moist chamber, then washed again 1 to 6 times, preferably 3 times, and eventually air-dried. The last washing should be carried out with demineralized water.

Microscopic evaluation of the preparation so treated is effected according to methods known to experts for immuno-fluorescence microscopy, for example according to Wick, Baudner, Herzog, Immunfluoreszenz, Beiträge zur Theorie und Praxis, Medizinische Verlagsgesellschaft. mbH, Marburg, 1976.

2. Proof of anti-nuclear antibodies

The proof of anti-nuclear antibodies is carried out in a manner corresponding to that used for the proof of anti-mitochondrial antibodies. In this case, however, fixed hypernephroma cells are advantageously used instead of air-dried unfixed hypernephroma cells.

A suitable method is fixation with acetone (Gell, Coombs, Jachmann, Clinical aspects of Immunology, Blackwell 1975, page 1122).

The following Example illustrates the invention:

EXAMPLE

A tumor tissue of a hypernephroma (hypernephroidal carcinoma) is isolated under sterile conditions during surgery and suspended in a tissue culture medium. The latter is a so-called Eagle medium in the Dulbecco modification having the usual composition:

| Amino-acids | mg/l |
|---|---|
| L-Arginine HCl | 84.0 |
| Glycine | 30.0 |
| L-Cystine | 48.0 |
| L-Histidine HCl . $H_2O$ | 42.0 |
| L-Isoleucine | 105.0 |
| L-Leucine | 105.0 |
| L-Lysine HCl | 146.0 |
| L-Methionine | 30.0 |
| L-Phenylalanine | 66.0 |
| L-Serine | 42.0 |
| L-Threonine | 95.0 |
| L-Tryptophane | 16.0 |
| L-Tyrosine | 72.0 |
| L-Valine | 94.0 |
| Vitamins | mg/l |
| D-Ca-Pantothenate | 4.00 |
| Choline-Chloride | 4.00 |
| Folic acid | 4.00 |
| i-Inositol | 7.20 |
| Nicotinamide | 4.00 |
| Pyridoxal-HCl | 4.00 |
| Riboflavin | 0.40 |
| Inorganic salts and other adjuvants: | |
| $CaCl_2$ | 200.00 |
| KCl | 400.00 |
| $MgSO_4 . 7H_2O$ | 200.00 |
| NaCl | 6400.00 |
| $NaHCO_3$ | 3700.00 |
| $NaH_2PO_4 . 2H_2O$ | 124.00 |
| $Fe(NO_3)_3 . 9H_2O$ | 0.10 |
| Glucose | 4500.00 |
| Phenol red | 15.00 |
| Sodium bicarbonate | 3.700 |

| -continued | |
|---|---|
| Penicillin | 10.000 IE |
| Streptomycin | 10.000 µg |

The tumor tissue is further treated within a few hours. In this process, the tissue which does not belong to the hypernephroma tissue is removed as much as possible and the undestroyed tumor tissue is further treated, also under sterile conditions, in a tissue culture medium which is likewise maintained in all of the following process steps. A piece of about 1 $cm^3$ of the tumor tissue is then comminuted mechanically to pieces of an edge length of about 1 mm and these pieces are suspended in 30 ml of Puck's salt solution (Puck's saline A).

Puck's salt solution has the following composition:

| NaCl | 8.00 g |
|---|---|
| KCl | 0.40 g |
| $NaHCO_3$ | 0.35 g |
| Glucose | 1.00 g | in 1 liter of distilled water.

The solutions used from hereon are heated to 37° C.

The suspension is stirred for 5 minutes with a magnetic stirrer in a trypsinization bottle according to Rappaport (Bull. World Health Organ. 14: 147, 1956; producer: Bellco Glass Inc., Vineland N.J., U.S.A., Cat. No. 1966). The supernatant is rejected and 30 ml of collagenase solution (10 mg of collagenase, Serva Heidelberg, in 20 ml of PBS without Ca and Mg having the following composition: NaCl 8.0 g, KCl 0.2 g, $Na_2HPO_4.12H_2O$ 2.9 g, $KH_2PO_4$, 0.2 g in 1 liter of distilled water) are added. The whole is stirred for 15 minutes. The supernatant is isolated by decanting it into a glass tube for centrifugation. 30 ml of a 0.25% strength solution of trypsin are added to the sediment and the whole is stirred for 15 minutes. Composition of the trypsin solution: 5 ml of trypsin (Difco 1:250), 5% strength in 100 ml of Puck's saline A, pH 8–8.5. The whole is stirred for 15 minutes and the supernatant is isolated and again stirred with a trypsin solution. The supernatants are centrifuged each time at 200×g and the cell sediment so obtained is suspended in 20 ml of Dulbecco's medium (cf. above) with addition of 20% of fetal calf serum. The cell concentration is adjusted to $5 \times 10^5$ cells per 1 milliliter and then 10 ml portion of the suspension are seeded in suitable Petri dishes of polystyrene (diameter 10 cm, Messrs. Greiner, Nürtingen). The dishes are incubated at 37° C. in a moist atmosphere in an incubator filled with $CO_2$-gas.

After development of the primary culture with formation of a closed monolayer, the cells of the primary culture are removed from the bottom of the Petri dishes and separated with the aid of the above-mentioned trypsin solution, suspended in a tissue culture medium, diluted to the desired cell number and again distributed in other Petri dishes. One Petri dish with full growth, permits the propagation of 3–4 new dishes for the next passage. The duplication time of the cells is about 18 hours. The medium in the culture dishes is renewed every 2–3 days.

After successfull propagation over 10 passages, cultures can be established on slides. For this purpose, cells are isolated from cultures by trypsination, adjusted in a tissue culture medium to a concentration of $1-2 \times 10^6$ cells per ml and distributed dropwise (1 drop about 20 μl) on previously prepared slides in such a manner that 1 drop is sufficiently distant from the next drop. For this purpose, there may be used, for example, slides with a light-impermeable black color coating having circular, clear spots into which the cells are placed.

Thus, the cells from one drop settle down in the area of this drop by sinking down in this drop and they spread on the glass of the slide and grow thereon. To achieve this, the slide must be kept in a moisture-saturated atmosphere under 5–10% $CO_2$-in air, at 37° C., for 4–6 hours, without movement.

The slide is then cultivated for a further 12–18 hours, immersed in a tissue culture medium. In general, a circular monolayer of hypernephroma cells having a diameter of 4–5 mm is formed.

The slides are then removed from the tissue culture medium and air-dried at room temperature.

A. Proof of anti-mitochondrial antibodies

The serum to be tested, which may contain anti-mitochondrial antibodies, is diluted with a physiological NaCl-solution, containing 0.1% of albumin, in a geometrically graded series (for example, 1:1, 1:2, 1:4, 1:8, 1:16, 1:32, 1:64, 1:128). One drop each of the respective dilutions is dropped each time on the circular cell monolayers adhering to the slides. The slides coated in such a manner with different dilutions are stored in a moist chamber (steam-impermeable box, the bottom of which is covered with liquid and which is provided with a screen, above the surface of the liquid, for holding the slides in horizontal position), for 30 minutes at room temperature (20° C.) and subsequently washed three times by immersing them in a vessel containing physiological NaCl-solution with 0.1% of albumin, removed after 5 minutes and correspondingly immersed in a second and third vessel. After the adhering liquid is allowed to drain off by storage for a short time (about 5 minutes) in an oblique position, the cell monolayers of the slide are over-coated with a drop of an antibody from rabbit labeled with fluorescein-isothiocyanate (FITC), directed against human immunoglobulins. The slides are then again stored in the moist chamber at 20° C. and subsequently washed three times as described above. As the dilution of the FITC-labeled antibody, a dilution is used which, when coated alone onto the cells, does not stain them unspecifically. After drying in air, the cell layers are covered with glycerin (free from own fluorescence) and with a cover glass and then evaluated microscopically with the aid of a fluorescence microscope, Messrs. Zeiss, with direct light, using an objective lens having a 25-fold, 40-fold and 100-fold magnification factor.

Those test series are considered positive which cause fluorescence of the mitochondria of the hypernephroma cells in the above described test.

B. Proof of anti-nuclear antibodies

The slides coated with circular cell monolayers are immersed for 10 minutes in acetone, then washed three times as described under A with a physiological NaCl-solution containing 0.1% albumin and dried in air. The dilution of the serum containing the anti-nuclear antibody, coating on the slides, incubation in the moist chamber, washing, coating with the FITC-labeled antibody, incubation, washing, air-drying, glass covering and microscopic evaluation are carried out as described under A.

Test sera in which the cell nuclei are spotted homogeneously or differently or in which the nuclear membrane or the nucleoli are fluorescing are considered positive.

What is claimed is:

1. A method for testing for the presence of anti-mitochondrial antibodies which comprises coating air-dried unfixed hypernephroma cells with an isotonic salt solution of the antibody to be tested, incubating the coated cells for 10 minutes to 2 hours in a moist chamber, then washing the cells with an isotonic salt solution and coating them with a fluorescently-labeled antibody directed against antigen-determinants of the antibody sought for, incubating the cells for 10 minutes to 2 hours in a moist chamber, washing at least once with demineralized water, and examining the cells by immunofluorescence microscopy, whereby fluorescence of the mitochondria of the hypernephroma cells is considered a positive finding of said anti-mitochondrial antibodies.

2. A method for testing for the presence of anti-nuclear antibodies which comprises coating fixed hypernephroma cells with an isotonic salt solution of the antibody to be tested, incubating the coated cells for 10 minutes to 2 hours in a moist chamber, then washing the cells with an isotonic salt solution and coating them with a fluorescently-labeled antibody directed against antigen-determinants of the antibody sought for, incubating for 10 minutes to 2 hours in a moist chamber, washing at least once with demineralized water, and examining the cells by immunofluorescence microscopy, whereby a homogeneous or differentiated spotting of the cell nuclei or fluorescence of the nuclear membrane or nucleoli is considered a positive finding of said anti-nuclear antibodies.

* * * * *